(12) United States Patent
Lichten

(10) Patent No.: US 8,835,406 B2
(45) Date of Patent: Sep. 16, 2014

(54) TREATMENT OF REYNAUD'S DISEASE

(71) Applicant: Edward M. Lichten, Birmingham, MI (US)

(72) Inventor: Edward M. Lichten, Birmingham, MI (US)

( * ) Notice: Subject to any disclaimer, the term of this patent is extended or adjusted under 35 U.S.C. 154(b) by 62 days.

(21) Appl. No.: 13/745,038

(22) Filed: Jan. 18, 2013

(65) Prior Publication Data

US 2014/0031311 A1    Jan. 30, 2014

Related U.S. Application Data

(60) Provisional application No. 61/587,684, filed on Jan. 18, 2012.

(51) Int. Cl.
*A61K 31/728* (2006.01)

(52) U.S. Cl.
CPC .................................. *A61K 31/728* (2013.01)
USPC ........................................................... 514/54

(58) Field of Classification Search
None
See application file for complete search history.

(56) References Cited

FOREIGN PATENT DOCUMENTS

WO    WO 2010/085123    *   7/2010

OTHER PUBLICATIONS

Williams, S. et al "Changes in skin physiology and clinical appearance . . . " J. Cosmetic Dermatology (2009) vol. 8, 216-225.*

* cited by examiner

*Primary Examiner* — Leigh Maier
(74) *Attorney, Agent, or Firm* — The Weintraub Group, P.L.C.

(57) ABSTRACT

A method of treating a patient inflicted with Reynaud's Disease including the step of injecting into the back of the patient's hand an effective amount of a hyaluronic product, thereby creating a glove-like insulation to decrease the blood vessel vasospasm.

1 Claim, No Drawings

TREATMENT OF REYNAUD'S DISEASE

CROSS REFERENCE TO RELATED APPLICATION

This application claims the benefit of U.S. Provisional Application 61/587,684, which was filed on Jan. 18, 2012, the disclosure of which is hereby incorporated by reference.

BACKGROUND OF THE INVENTION

1. Field of the Invention

The present invention pertains to the treatment of certain medical conditions. More particularly, the invention concerns the treatment of temperature precipitated medical conditions. Even more particularly, the present invention concerns the treatment of Reynaud's Disease.

2. Prior Art

As is known to those skilled in the art to which the present invention pertains, Reynaud's Disease is a condition that affects approximately 5% of men and 8% of women. Typically the condition occurs in Northern or cold climates. The condition is precipitated by a cold environment which causes an exaggerated vasoconstrictive response that usually turns the fingertips, hands, as well as potentially the toes, nose, and ears red, white, or blue. The disease, which results in a decrease in blood flow to the extremities, is painful and has the potential, in extreme cases, of causing gangrene and even amputation.

In addition, observations have shown that the order of changing color is not the same for all people or that everyone experiences all three colors. It has also been observed that if circulation improves, the affected areas may turn red, throb, tingle, or swell. Occasionally, an attack affects just one or two digits and not necessarily always the same digits as the disease repeats or reappears.

As noted above, typically, exposure to cold temperatures causes the Reynaud's Disease conditions. However, stress has also been shown to be a cause.

In addition, Reynaud's Disease has been broken into two categories. There is Primary Reynaud's Disease which is Reynaud's Disease without an underlying disease or associated medical problem that could provoke vasospasm.

Secondary Reynaud's Disease is a phenomenon caused by an underlying problem such as scleroderma, lupus, rheumatoid arthritis, and the like. Even smoking, which constricts blood vessels, has been associated with Secondary Reynaud's Disease.

To date, the most prevalent treatments for Primary Reynaud's Disease have taken on environmental change such as avoidance of cold, smoking cessation, and relief of stress. Drugs may be used. Ordinarily the drugs are vasodilators including calcium channel blockers, amlodipine, felodipine or isradipine. Lesser drugs can include, for example, prazosin, topical nitroglycerine paste, and pentoxifylline. The drug treatments are usually associated with Secondary Reynaud's Disease.

As can be seen from the above, the art has not disclosed an effective treatment in the heretofore Primary Reynaud's Disease other than alteration of the environmental situation which causes the disease.

It is to this to which the present invention is directed.

DESCRIPTION OF THE PREFERRED EMBODIMENT

In accordance with the present invention, Reynaud's Disease is treated by injecting into the back of the hand an effective amount of a hyaluronic product, namely hyaluronic acid, to create a glove-like insulation to decrease the blood vessel vasospasm, and to minimize and overcome the effects of the Reynaud's Disease.

Although not wishing to be bound by any theory, it appears that the thinner skin or dorsum of a hand is where major vessels reside and where the temperature loss occurs. The palms, being on the ventral surface where the skin is thicker and the fat pads on the hands are located, are relatively protected from the conditions which cause the Reynaud's Disease.

It has now been observed that by injecting the hyaluronic acid directly into the dorsum skin, the effects of Reynaud's Disease can be overcome, and the effect may continue for up to one year. The acid may be used alone or in admixture with a high potency topical anesthetic, such as novocaine, lidocaine, and the like. In preparing the admixture product, generally, from about 1 part by weight of the acid and about 2 to about 4 parts anesthetic are used. When used with or without a local anesthetic, generally about 1 cc to 3 cc's of acid is used.

In injecting the hyaluronic acid it is done in a linear fashion following the caudad-cephalid direction of the ligaments. When used alone, because of the sensitivity of the area to be treated, a topical anesthetic is applied in sufficient amounts and for a sufficient period of time to numb the skin. Thereafter, the hyaluronic acid is injected into the subcutaneous skin. In order to effectively abate the affects of Reynaud's Disease, the injections are provided or used, typically, in a single dose injection about once a year.

For a more complete understanding of the present invention, reference is made to the following representative protocol for determining the efficacy of the present invention.

Example 1

At the outset it should be noted that thermography is an easy, non-invasive tool for recording surface temperatures used to assess Raynaud's phenomenon, scleroderma, peripheral nerve injury and reflux sympathetic dystrophy. Various studies have confirmed the existence of thermal symmetry in healthy individuals. It is recognized that differences in skin temperature of more than 0.5° C. before and after any intervention or treatment of the hand or extremity suggests a change in underlying pathophysiology.

Cold intolerant persons, such as those with Raynaud's phenomenon, have lower skin temperatures and react abnormally to cold stress testing. Skin temperatures correlate with blood flow and with sympathetic nerve damage. Cold stress testing can show otherwise subclinical thermal asymmetry.

Protocol: Into a bath of cold water maintained at 11° C., are placed the feet of a person affected with Reynaud's Disease. After immersion for one minute, the feet are removed from the bath. The baseline thermographic color and temperature of the hands immediately after the feet are placed in the cold water bath are observed.

After removing the feet from the bath, one hand is injected with 2 cc's of hyaluronic acid after the dorsum has been treated with lidocaine. The feet are again immersed in the cold water bath for an allotted time period of 1 minute. The feet are then removed and the color differences between the right hand and the left hand are observed. Then the other hand is injected with hyaluronic acid, again, after having the anesthetic topically applied thereto.

Thereafter, the feet again are immersed in the cold water bath for a third time and removed per the three minute protocol. The thermographic color changes of the hands are then observed. In this instance it is shown that the color changes are dramatically less affected and the patient reports, on a visual analog scale a decrease in pain.

Example 2

Following the procedure of Example 1, four patients, three women and one man, known to have chronic complaints of hand cold intolerance were subjected to the protocol. The three women and one man were non-smokers nor overweight. All were relatively healthy. The age of the male was 22; the mean age of the three women was 55 years of age. All the women were menopausal and on estrogen replacement therapy.

Each patient had both hands tested for cold provocation. The patients were acclimated indoors for at least 30 minutes at an ambient room temperature of 23-25° C. A Model A325 Flir Systems, Inc. infrared camera was calibrated to detect temperature differences of 0.1° C. The thermographic images were videotaped and analyzed.

The patients were seated comfortably and the initial temperature recordings were taken by the videocamera of both the front (palm) and back (dorsum) of the hands. After baseline themographic readings were completed, the patient's feet were submerged in a 11° C. water bath for 1 minute.

The feet were then air dried for about 1 minute and, then, thermographic videotape reading of the ventral and dorsal surfaces of the hands resumed.

Mean baseline temperatures were computed from still-life computer images. The measurements were computed from pictures taken both before the cold provocation, after the cold water testing. A standard color palette with a spectrum in which a blue-green color indicates colder and indicates colder and a red-orange color indicates warmer and white indicates warmest was used. The right hand of each patient volunteer was injected with 1 cc hyaluronic acid and the testing repeated both before the cold provocation and after injection and, then, after the subsequent cold water testing.

The thermographic results before and after the cold challenge were compared to the before and after cold challenge after the injections. The significance of the difference between the injected and non-injected hands was reported as individual data.

The mean difference in temperature before and after the cold challenge was 3° C. (1.5° C., 3° C., 5° C.). The untreated hands had no significant temperature variance from the first 'before' to second 'before' or 'after' to 'after' in the injected hand and non-injected hand. The pattern of temperature improvement after hyaluronic acid injections was similar in the responders although the absolute temperature varied from finger to finger. Pair wise testing of digital temperatures between hands showed no significant difference (Wilcoxson signed ranks test). This was done for each finger separately, by grouping the two radial fingers together and for all fingers together.

The injection of hyaluronic acid to the dorsum of the hand of individuals who document cold stress testing has shown fingertip warming upon repeated cold stress testing.

While the treatments disclosed herein are directed to Primary Reynaud's Disease it is believed to be equally effective in Secondary Reynaud's Disease.

I claim:

1. A method of treating a patient inflicted with Reynaud's Disease including the step of injecting into the back of the patient's hand an effective amount of hyaluronic acid, thereby creating a glove-like insulation to decrease the blood vessel vasospasm.

* * * * *